(12) United States Patent
Pavelka, Jr. et al.

(10) Patent No.: US 6,423,545 B1
(45) Date of Patent: Jul. 23, 2002

(54) UNMARKED DELETION MUTANTS OF MYCOBACTERIA AND METHODS OF USING SAME

(75) Inventors: Martin S. Pavelka, Jr., Rochester; William R. Jacobs, Jr., City Island, both of NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/350,047

(22) Filed: Jul. 8, 1999

(51) Int. Cl.⁷ .............................................. C12N 15/00
(52) U.S. Cl. ..................... 435/477; 435/471; 435/481; 435/253.1
(58) Field of Search ........................... 514/44; 435/7.32, 435/69.1, 253.1, 477, 481, 320.1, 6, 252.3, 471, 476

(56) References Cited

U.S. PATENT DOCUMENTS 5,843,664 A * 12/1998 Pelicic et al. ................... 435/6

FOREIGN PATENT DOCUMENTS

WO    WO 97/14805    *   4/1997

OTHER PUBLICATIONS

Pelicic et al. FEMS Microbiology Letters. 144: 161–166, 1996.*
Guleria et al. Nature Medicine. 2(3): 334–337, Mar. 1996.*
Gheorghiu M. International Journal of Immunopharmacology. 16(5–6): 435–44, May 1994.*
Roche et al. Trends in Microbiology. 3(10): 397–401, Oct. 1995.*
Pavelka et al. Journal of Bacteriology. 178(22): 6496–6507, Nov. 1996.*
Maes. Medical Hypotheses. 53(1): 32–39, 1996.*
U.S. Trademark Electronic Search System (TESS), Word Mark: Tween.*

* cited by examiner

Primary Examiner—James Martinell
(74) Attorney, Agent, or Firm—Amster, Rothstein & Ebenstein

(57) ABSTRACT

Disclosed is a recombinant slow-growing mycobacterium comprising at least one mycobacterial gene containing an unmarked mutation, where an "unmarked mutation" is a mutated nucleotide sequence introduced into a mycobacterium where the introduced mutated nucleotide sequence does not contain a selectable marker, such as a gene conferring antibiotic resistance to the recombinant mycobacterium incorporating the mutated nucleotide sequence. Also disclosed is a method for preparing a recombinant slow-growing mycobacterium comprising at least one mycobacterial gene containing an unmarked mutation, as well as a vaccine comprising a recombinant slow-growing mycobacterium having at least one mycobacterial gene containing an unmarked mutation dispersed in a physiologically acceptable carrier. Further disclosed is a method of treating or preventing tuberculosis in a subject comprising administering the vaccine of the present invention in an amount effective to treat or prevent tuberculosis in the subject.

10 Claims, 3 Drawing Sheets

UNMARKED DELETION MUTANTS OF MYCOBACTERIA AND METHODS OF USING SAME

STATEMENT OF GOVERNMENT INTEREST

This invention is supported by NIH Grant Nos. AI26170 and AI33696. As such, the U.S. Government has certain rights in this invention.

BACKGROUND OF THE INVENTION

*Mycobacterium tuberculosis*, the agent of tuberculosis, is the leading cause of death in adults worldwide (14). The emergence of drug resistant strains (48) and the problems associated with tuberculosis in HIV-infected populations (18) have brought tuberculosis research to the forefront. The development of genetic techniques to study the biology of the organism is an important goal of mycobacterial research.

Considerable effort has gone into the development of allelic exchange methods to selectively disrupt genes of various mycobacterial species. Several groups have used either small linear DNA fragments (4, 25, 43), long linear DNA fragments (5), or suicidal plasmids, (37, 44) (9, 27, 39, 41, 42) to achieve allelic exchange in both fast and slow-growing mycobacteria. Slow-growing mycobacteria such as *M. tuberculosis* and *M. bovis* BCG can integrate exogenous DNA into their chromosome by both illegitimate and homologous recombination (2, 25). Allelic exchange in fast-growing mycobacteria such as *M. smegmatis* is easier than in the slow-growing species; this has led to the idea that the homologous recombination machinery of slow-growing mycobacteria is rather inefficient (32).

Thus far, the only mutants constructed in the slow-growing mycobacterial species are those with genes disrupted with an antibiotic marker. However, in many cases an antibiotic marker may not be desirable. It may not be known whether or not a gene is essential and targeted disruption does not let one ascertain essentiality. The failure to obtain a mutant might be due to the failure of the methodology and not to the essentiality of the gene. Furthermore, the possibility of polar effects from an inserted antibiotic marker can prevent the disruption of a non-essential gene if that gene is located in an operon upstream of an essential gene. Also, there are a limited number of antibiotic resistance genes available for use in mycobacteria and making a marked mutation excludes one antibiotic from further consideration. In addition, mutants that are potential vaccine candidates should not contain antibiotic resistance determinants.

An ideal allelic exchange system is one that can be used for the exchange of unmarked deletion alleles as well as alleles with point mutations. Constructing knockout mutants by in-frame deletions would negate the concerns with using a targeted disruption method. Such mutants are antibiotic sensitive, cannot revert, and the mutations should not be polar on the expression of downstream genes. By extension, the same technique could be used for allelic exchange of point mutations, allowing for a finer dissection of gene function. This allelic exchange methodology, utilizing a plasmid unable to replicate in the organism of interest and selectable and counter-selectable markers (15), has been successfully used in *M. smegmatis* (27, 41). The inventors sought to determine if such an allelic exchange methodology would reproducibly work for the slow-growing mycobacteria, such as *M. bovis* BCG and *M. tuberculosis*.

The inventors describe herein a new mycobacterial suicide plasmid for allelic exchange of unmarked mutations utilizing sacB sucrose counter selection. This counter selectable marker was previously reported to work in mycobacteria, including *M. tuberculosis* and *M. bovis* BCG (40) (42) (9). However, the previously described mycobacterial sacB vector systems were used for allelic exchange of genes disrupted with an antibiotic resistance marker. The present invention demonstrates the reproducibility of this system for allelic exchange of unmarked deletions in the chromosome of *M. smegmatis*, *M. bovis* BCG and *M. tuberculosis*. The inventors have also constructed lysine auxotrophs of these three organisms by allelic exchange of lysA, the gene encoding meso-diaminopimelate decarboxylase, the last enzyme in the lysine biosynthetic pathway (52). To the best of the inventors' knowledge, this is the first report of the construction of unmarked deletion mutations in the genome of slow-growing mycobacteria.

SUMMARY OF THE INVENTION

The present invention discloses a slow-growing recombinant mutant mycobacterium comprising at least one mycobacterial gene containing an unmarked mutation. The invention further provides a method for preparing the recombinant mutant mycobacterium of the present invention comprising introducing a vector into a slow-growing mycobacterium, where said vector comprises a selectable marker, a counter selectable marker, and an unmarked mutant mycobacterial gene, culturing the slow-growing mycobacterium and selecting for primary recombinants incorporating the selectable marker. The primary recombinants are then cultured, and secondary recombinants that have lost the counter selectable marker are selected for, followed by isolation of the secondary recombinants incorporating the desired unmarked mutant mycobacterial gene.

Also provided is a vaccine comprising the slow-growing recombinant mutant mycobacterium of the present invention contained in a physiologically acceptable carrier, as well as a method of treating or preventing tuberculosis in a subject comprising administering the vaccine of the present invention in an amount effective to treat or prevent tuberculosis in the subject.

DETAILED DESCRIPTION OF THE INVENTION

Figure 1:
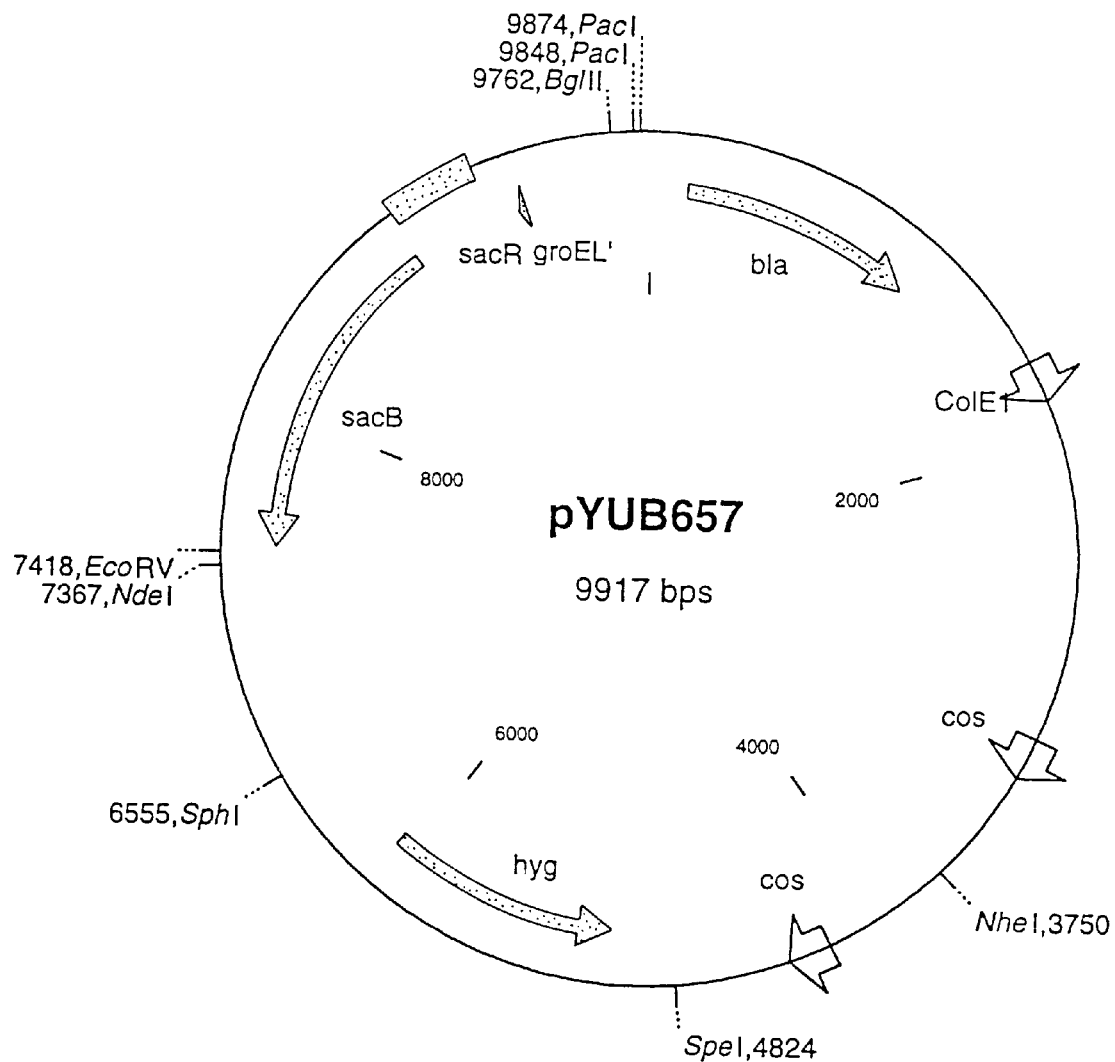
FIG. 1 depicts a map of the suicide vector pYUB657. The vector pYUB657 cannot replicate in mycobacteria, but has the ColE1 origin of replication for *E. coli*. The $P_{groEL}$-sacB cassette is indicated along with the sacR regulatory region (50). The vector has the bla gene, conferring resistance to ampicillin in *E. coli* and the hyg gene, conferring resistance to hygromycin in mycobacteria. This vector is also a double cos, PacI-excisable cosmid cloning vector (5). Useful cloning sites are indicated.

The present invention provides a method for yielding recombinant unmarked mutants of mycobacteria, wherein the recombinant mutant mycobacteria comprises at least one mycobacterial gene containing an unmarked mutation. As used herein, an "unmarked mutation" is a mutated nucleotide sequence (i.e., a mutant DNA substrate) that is homologous to and replaces a wildtype nucleic acid sequence of the mycobacteria via homologous recombination, where said mutant DNA substrate does not contain a selectable marker, such as a gene conferring antibiotic resistance to the recombinant mycobacterium incorporating the mutated nucleotide sequence. The term "recombinant unmarked mutant mycobacteria" as used herein means that the recombinant unmarked mutant mycobacterium comprises at least one unmarked mutation, such that the expression or function of the mutant DNA substrate incorporated into the recombinant mycobacterium is varied with respect to the non-mutated nucleotide sequence in the parent strain. The method of the present invention is particularly suited for generating mutants via allelic exchange in *Mycobacterium tuberculosis* complex organisms, preferably strains of *M. tuberculosis, M. bovis* and Bacille-Calmette-Geurin (BCG), which are slow-growing mycobacteria, as well as in other slow growing mycobacteria, although the method may be used with non-tuberculosis fast-growing mycobacteria commonly encountered in biological samples isolated from human subjects, e.g., *M. avium-intracellulare, M. kansasii, M. xenopi, M. scrofulaceum, M. simiae, M. szulgai, M. gordonae, M. gastri, M. smegmatis,* and *M. chelonae*.

The method for preparing a recombinant unmarked mutant of the present invention comprises introducing a vector into a slow-growing mycobacterium, where said vector comprises a selectable marker, a counter selectable marker, and a mutant DNA substrate for allelic exchange, then growing the mycobacterium and selecting for primary recombinants incorporating the selectable marker, then culturing the primary recombinants incorporating the selectable marker and selecting for secondary recombinants that have lost the counter selectable marker, and isolating the secondary recombinants comprising the desired unmarked mutation. The method of the invention may also be used to produce recombinant unmarked mutant mycobacteria that are fast-growing mycobacteria, including recombinant mutant strains of *M. smegmatis* or *M. avium*, but is preferably used to produce recombinant unmarked mutant strains of slow-growing mycobacteria, and more preferably, recombinant unmarked mutants of *M. tuberculosis* or *M. bovis* BCG strains.

The vector of the present invention is a plasmid which is unable to replicate in mycobacteria (i.e., a suicide plasmid), having a selectable marker and counter selectable marker on the plasmid backbone. Selectable marker genes which may be included on the plasmid are well known in the art and include, but are not limited to, genes encoding resistance to antibiotics, including carbenicillin, viomycin, thiostrepton, ampicillin, tetracyline, hygromycin, kanamycin or bleomycin. In a preferred embodiment of the invention, the selectable marker genes included on the vector are genes encoding for ampicillin and hygromycin resistance. The counter selectable marker which is included on the vector confers susceptibility to a specific agent, and preferably is one of the rpsL, pyrF, or sacB genes, and more preferably is the sacB gene encoding for levansucrase and conferring susceptibility to sucrose.

The mutant DNA substrate for allelic exchange may be of any origin, but is preferably from a mycobacterium. In a preferred embodiment of the invention, the mutated DNA substrate for allelic exchange is from a mycobacterium and is homologous to a wildtype nucleic acid sequence of the mycobacterium in which it is desired to introduce the mutated DNA substrate in lieu of the wildtype nucleic acid sequence.

The DNA substrate for allelic exchange contains the mutation of interest, which through allelic exchange, is introduced into and replaces the homologous region of the mycobacterium nucleic acid. As used herein, "mutated DNA substrate" refers to the nucleotide sequence for at least one allele that has been modified by addition, substitution or deletion of at least one nucleotide, and lacks any selectable marker. In a preferred embodiment of the invention, the mutated DNA substrate comprises a deletion or point mutation of the wildtype nucleic acid sequence. Mutations, including but not limited to deletion, point, substitution, or insertion mutations, may be generated by any number of methods known in the art, including but not limited to treatment with restriction endonucleases, inverse PCR, subcloning techniques and other methods of in vitro mutagenesis. The wildtype nucleic acid sequence may encode a protein or polypeptide, and in a preferred embodiment of the invention encodes an enzyme essential in the biosynthetic pathway of a nutrient, structural or cell wall component of the mycobacterium, or an amino acid, such as lysine, leucine, methionine, etc. It is also within the confines of the present invention that the wildtype nucleic acid of the mycobacterium may comprise an operon or cluster of alleles encoding a number of proteins or polypeptides, or one or more promoters, enhancers or regulators that are involved in the expression and translation of mycobacterial proteins and polypeptides. In a preferred embodiment of the invention, the wildtype nucleic acid comprises the lysA gene.

The suicide vector, comprising a selectable marker, a counter selectable marker, and the mutant DNA substrate for allelic exchange, is introduced to the mycobacteria using any suitable method known in the art, including by electroporation. Primary recombinants incorporating the selectable marker are directly selected for using the appropriate agent, for instance, by exposing the mycobacterium to hygromycin and obtaining Hyg$^r$ clones where the selectable marker confers resistance to hygromycin. Secondary recombinants that have lost the counter selectable marker are directly selected for by using the appropriate agent, for instance, by exposing the mycobacterium to sucrose and obtaining suc$^r$ clones where the counter selectable marker is sacB. Once suspected secondary homologous recombinants comprising the desired unmarked mutation are isolated, the unmarked mutation genotype may be confirmed by methods known in the art, such as PCR screening or Southern blot analysis.

The method of the present invention may be used to generate numerous strains of auxotrophic recombinant unmarked mutant mycobacteria that are auxotrophic for a particular nutrient or nutrients by reason of the substitution via allelic exchange of a wildtype nucleic acid sequence of a mycobacterium with a mutated DNA substrate. As used herein, the term "auxotrophic recombinant unmarked mutant mycobacterium" is defined as a mycobacterium having an unmarked mutation resulting in the nutritional requirements of the mycobacterium being altered. For example, some auxotrophic mutants are unable to synthesize amino acids, or may require specific amino acids that are not needed by the parental or prototrophic strain. Specific auxotrophic recombinant unmarked mutant mycobacteria of the present invention include slow-growing mycobacteria which are auxotrophic for lysine, although other auxotrophic recombinant unmarked mutants of slow growing mycobacteria are provided for, including recombinant unmarked mutants that are auxotrophic for leucine, threonine, methionine, etc. Preferably, the auxotrophic recombinant unmarked mutant mycobacteria are strains of *M. bovis* BCG or *M. tuberculosis*, but the invention is not limited to these species of mycobacteria. In a specific embodiment of the invention, the auxotrophic recombinant unmarked mutant mycobacteria that is auxotrophic for lysine comprises an unmarked mutation of the lysA gene.

The present invention provides a vaccine comprising an auxotrophic recombinant unmarked mutant mycobacterium. The invention also provides a method of treating or preventing tuberculosis in a subject comprising administering the vaccine of the present invention in an amount effective to treat or prevent tuberculosis in the subject. In this regard, the vaccine containing the recombinant unmarked mutant slow-growing mycobacteria of the present invention may be administered in conjunction with a suitable physiologically acceptable carrier. Mineral oil, alum, synthetic polymers, etc., are representative examples of suitable carriers. Vehicles for vaccines and therapeutic agents are well within the skill of one skilled in the art. The selection of a suitable vaccine is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration.

Further, mycobacteria have well known adjuvant properties and so are able to stimulate a subject's immune response to respond to their antigens with great effectiveness. Their adjuvant properties are especially useful in providing immunity against pathogens in cases where cell mediated immunity is critical for resistance. In addition, the mycobacterium stimulates long-term memory or immunity and thus a single inoculum may be used to produce long term sensitization to protein antigens. The vaccine of the present invention may be used to prime long-lasting T-cell memory, which stimulates secondary antibody responses which will neutralize infectious agents or toxins, e.g., tetanus and diptheria toxins, pertussis, malaria, influenza, herpes virus and snake venom.

In addition, the recombinant unmarked mutant mycobacterium of the present invention that is auxotrophic for lysine may be used in the construction of DAP auxotrophs (peptidoglycan mutants).

The present invention is described in the following Experimental Details Section which is set forth to aid in the understanding of the invention, and should not be construed to limit in any way the scope of the invention as defined in the claims which follow thereafter.

Experimental Details Section

A) Materials and Methods

Bacterial strains and culture methods: The bacterial strains used are listed in Table 1. The genetic nomenclature for strains bearing an integrated suicide plasmid (DUP) is as previously described (37). *E. coli* cultures were grown in LB (Luria-Bertani) broth or on LB agar (DIFCO). Mycobacterial cultures were grown in Middlebrook 7H9 broth (DIFCO) with 0.05% Tween-80® (polyoxyethylenesorbitan monooleate), or on 7H9 medium solidified with 1.5% agar or on Middlebrook 7H10 or 7H11 media (DIFCO). All cultures were incubated at 37° C. All Middlebrook media were supplemented with 0.2% (v/v) glycerol and with 1X ADS (0.5% bovine serum albumin, fraction V (Boehringer Mannheim), 0.2% dextrose, and 0.85% NaCl) for *M. bovis* BCG and *M. tuberculosis* cultures. Basal media were 7H9 and 7H10 supplemented as described above. Sucrose was used in the medium at a concentration of 2% (w/v), added after the medium was autoclaved and cooled to 55° C. Casamino acids (acid-hydrolyzed casein, DIFCO) was used at a concentration of 0.2 % (w/v). Individual amino acids were obtained from Sigma Chemical (St. Louis, Mo.) and used at a concentration of 40 μg/ml, unless indicated otherwise. The lysine analog S-(β-aminoethyl)-L-cysteine (AEC) was obtained from Sigma Chemical, dissolved in water and used at a concentration of 3 mM. When required, the following antibiotics were used at the specified concentrations; carbenicillin (50 μg/ml; *E. coli*), kanamycin A monosulfate (25 μg/mil; *E. coli, M. smegmatis, M. bovis* BCG), hygromycin B (50 μg/ml; *E. coli, M. bovis* BCG, and *M. tuberculosis*, 150 μg/ml; *M. smegmatis*). Hygromycin B was purchased from Boehringer Mannheim (50 mg/ml in phosphate buffered saline), all other antibiotics were purchased from Sigma Chemical. It was often found that pYUB412 and pYUB405-based plasmids were only stable in *E. coli* using both carbenicillin and hygromycin at 50 μg/ml in solid and liquid media. *M. smegmatis* plates were incubated for 3–5 days, while *M. bovis* BCG and *M. tuberculosis* plates were incubated for 3–4 weeks. *M. smegmatis* liquid starter cultures were inoculated from plates into 10 ml of medium in 30 ml plastic media bottles, grown for 1–2 days on a shaker platform at 100 rpm and then subcultured 1:100 in fresh media within 250 ml glass baffle flasks. *M. bovis* BCG and *M. tuberculosis* starter cultures were inoculated using 1 ml frozen stocks in 10 ml of media in 30 ml plastic media bottles and incubated for 5–7 days on a shaker platform at 100 rpm. Larger cultures were inoculated from the starter cultures at a 1:50 dilution in 50 ml or 100 ml of medium within 490 cm$^2$ roller bottles (Corning) and incubated on a roller apparatus at 8 rpm for 5–7 days. For growth curves, mid to late exponential phase cultures were centrifuged, washed with fresh media lacking supplements, and the cells resuspended appropriately and inoculated into test media. Samples of *M. tuberculosis* and BCG cultures were mixed 1:1 with 10% phosphate-buffered formalin and fixed for at least 1 hour prior to spectrophotometric measurement at O.D.$_{600}$.

DNA methodologies: DNA manipulations were done essentially as previously described (29). The plasmids used in this study are listed in Table 2. Plasmids were constructed in E. coli HB101 or DH5α cells and prepared by an alkaline lysis protocol (22). Plasmids used for recombination were purified using Qiagen columns as recommended by the manufacturer (Qiagen, Inc., Chatsworth, Calif.). DNA fragments used for plasmid construction were purified by agarose gel electrophoresis and recovered by absorption to glass fines (GeneClean, Bio 101, Vista, Calif.).

Genomic DNA was prepared either as previously described (23) or by a modified guandinium thiocyanate protocol (34). Briefly, the cells from a 10 ml culture are lysed with 1.3 ml of a 3:1 mixture of chloroform: methanol. The lysate is mixed with 1.3 ml of Tris-equilibrated phenol and a 2 ml of GTC solution (4 M guandinium thiocyanate, 0.1 M Tris pH 7.5, 0.5% sarcosyl, with β-mercaptoethanol added to a final concentration of 1% prior to use). The upper phase is collected after centrifugation and the genomic DNA precipitated with isopropanol. Southern blotting and hybridization were done as previously described (37). Oligonucleotides for sequencing and PCR were synthesized by the Albert Einstein College of Medicine oligonucleotide synthesis facility.

Cloning and sequencing of the M. smegmatis lysA operon: The inventors used a library of genomic DNA from wild-type M. smegmatis mc$^2$155 constructed in the cosmid vector pYUB412 to clone the lysA gene. The vector pYUB412 is an integration-proficient, PacI-excisable cosmid vector (6). This cosmid vector has the mycobacteriophage L5 attachment site (attP), the L5 integrase gene (int), and the hyg gene, conferring resistance to hygromycin. This vector efficiently integrates into the mycobacteriophage L5 attachment site (attB) of the mycobacterial chromosome and is stable (28). The pYUB412::mc$^2$155 library was electroporated into the strain MCK3037, a lysine auxotrophic mutant of mc$^2$155 generated by EMS mutagenesis (33). Transformants were selected on 7H10 media lacking lysine and Lys$^+$ clones screened for the hygromycin resistance marker carried on the cosmid vector backbone. One Lys$^+$ Hyg$^r$ clone was chosen for study and the genomic DNA insert within the integrated cosmid recovered by λ in vitro packaging (GigaPak III, Strategene). The recovery procedure is as follows: the library insert DNA is flanked by PacI restriction endonuclease sites present in the cosmid vector, and since PacI sites do not exist in mycobacterial genomic DNA (26), PacI digestion of the genomic DNA will release the cosmid insert DNA. This DNA fragment is re-packaged into PacI-digested arms of the cosmid vector pYUB412 by λ in vitro packaging, and a new cosmid (pYUB601) with the insert recovered in E. coli. The cosmid pYUB601 insert DNA was subcloned to a 4.4-kb EcoRI fragment bearing the lysA gene in plasmid pYUB604. The plasmid pYUB604, and two subclones, pYUB605 and pYUB607, were templates for DNA sequencing using the Applied Biosystems Prism Dye Terminator Cycle Sequencing Core kit with AmpliTaq DNA polymerase (Perkin Elmer) and an Applied Biosystems 377 automated DNA sequencer. Sequence data for both strands of the lysA operon of M. smegmatis were obtained from these subclones and by primer walking.

Construction of sacB suicide vector pYUB657: A 2.5-kb PstI fragment from the E. coli sacB vector pVCD442 bearing sacB and its upstream regulatory region sacR, were subcloned into the PstI site of the shuttle vector pMV261 downstream of the mycobacterial groEL (Hsp60) promoter, yielding the plasmid pYUB631. A 3.5-kb NotI-NheI fragment from pYUB631, bearing P$^{groEL}$-sacB was cloned into the cosmid vector pYUB405, resulting in the final construct, pYUB657 (see FIG. 1). The vector pYUB405 is a PacI-excisable cosmid vector unable to replicate in mycobacteria and encodes resistance to ampicillin and hygromycin (6).

Construction of the M. smegmatis ΔlysA4 suicide plasmid pYUB618: The plasmid pYUB604 was used as the template in an inverse PCR reaction to produce a deletion within the lysA gene. Oligonucleotide primers Pv44 (5'-CCCGTCGTACGTACGAACCAGGTTGCGC-3') (SEQ ID NO:1) and Pv45 (5'-CGAGTCGATACGTACTGCTGTGCCGCCC-3') (SEQ ID NO:2) were used at 50 pmol each in an inverse XL-PCR reaction in a Perkin Elmer 9600 temperature cycler with the following program: 95° C./5 min, 1 cycle; 93° C./1 min-68° C./5 min, 16 cycles; 93° C./1 min-68° C./5 min with ΔTh=15 sec, 12 cycles; 72° C./30 min. The reaction produced a 7.7-kb fragment with a 1.2-kb deletion within the lysA ORF (spanning nt positions 2051 . . . 3251 of GenBank accession AF126720) marked with a unique SnaBI site. The PCR product was gel purified, digested with SnaBI and self-ligated to yield the plasmid pYUB617. A 3.2-kb EcoRI fragment from pYUB617 bearing the ΔlysA4 allele was cloned into the PacI sites of the mycobacterial sacB suicide vector pYUB657, resulting in the M. smegmatis ΔlysA4 suicide plasmid pYUB618.

Construction of the M. bovis BCG/M. tuberculosis ΔlysA5:: res suicide plasmid pYUB668: The lysA gene of M. tuberculosis was originally cloned and sequenced by Anderson et al. (3). The plasmid pET3d.lysA contains the lysA gene of M. tuberculosis strain Erdman cloned by PCR using primers designed from the previously published sequence (3) (16). A 1.3-kb XbaI-BamHI fragment bearing the lysA gene was cloned from pET3d.lysA into the same sites in PKSI$^+$ to produce pYUB635. This plasmid was used as the template in an inverse PCR reaction with the oligonucleotide primers Pv7: (5-'GATAGCGGTCACGCGTCTCGTGCGCGGTGGA-3') (SEQ ID NO:3) and Pv8 (5-TCCGTACGATACGCGTCAGCCACATCGGTTCG-3') (SEQ ID NO:4) to generate a 95-bp deletion within the lysA gene marked with a unique MluI restriction endonuclease site. The inverse XL-PCR reaction was done using a Perkin Elmer 9600 temperature cycler and the program described above for plasmid pYUB617. The resulting 4.1-kb PCR product was gel-purified, digested with MluI and self-ligated to yield the plasmid pYIJB636. The lysA deletion was marked with the aph gene, conferring kanamycin resistance, by insertion of a specialized aph cassette via the unique MluI site to yield pYUB638. This specialized cassette has an aph gene flanked by two γδ resolvase sites from the E. coli transposon γδ (Tn1000) (20). The presence of the resolvase sites makes it possible to excise the antibiotic marker by expressing the γδ resolvase in mycobacteria after the cassette has been inserted into the mycobacterial chromosome (8). In the present case, however, the res-aph-res marker was removed from pYUB638 by resolvase excision in E. coli DH5α prior to introduction into mycobacteria (see below).

Figure 2A:
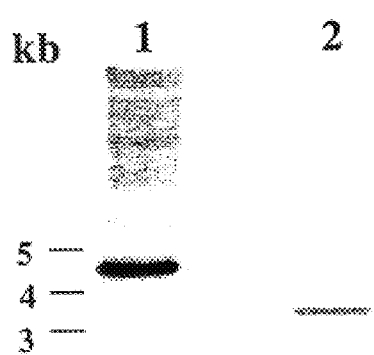
FIG. 2 illustrates Southern blots of genomic DNA from four mycobacterial lysA deletion mutants. Panel A depicts genomic DNA from wild-type *M. smegmatis* mc$^2$155 (Lane 1) and the *M. smegmatis* auxotroph mc$^2$1493 (Lane 2), digested with EcoRi and probed with a 3.3-kb EcoRI fragment from plasmid pYUB617, encompassing the ΔlysA4 allele. The wild-type fragment is the expected 4.4-kb, while the mutant has the expected 3.2-kb fragment. Panel B depicts genomic DNA from wild-type BCG substrain Pasteur (Lane 1), BCG substrain Pasteur auxotroph mc$^2$1604 (Lane 2), wild-type BCG substrain Connaught (Lane 3), BCG substrain Connaught auxotroph mc$^2$2519 (Lane 4), wild-type *M. tuberculosis* H37Rv (Lane 5), and *M. tuberculosis* H37Rv auxotroph mc$^2$3026 (Lane 6), digested with BssHII and probed with a lysA PCR product obtained from BCG Pasteur wild-type genomic DNA. Digestion of wildtype genomic DNA with BssHII splits the lysA gene over two fragments, one which is 1.1-kb in size, the other which is 1.2-kb. Digestion of genomic DNA from the deletion mutants yields the same 1.2-kb fragment seen in wild-type with a 0.9-kb fragment, corresponding to the deletion site, replacing the 1.1-kb fragment. The blots in Panel B show the expected shift in size of the 1.1-kb fragment down to 0.9-kb in all three mutants (Lanes 2, 4, and 8). The invariant 1.2-kb fragment shows a lower intensity in the blot due to a lower percentage of homology to the probe, relative to the 1.1 and 0.9-kb fragments.
Figure 2B:
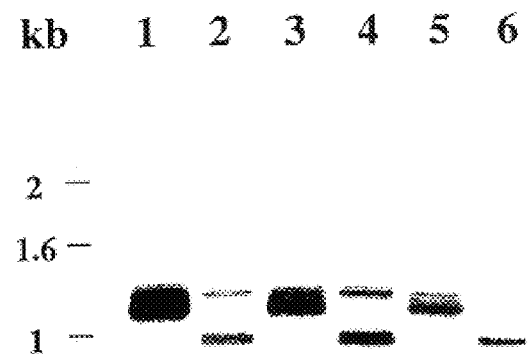
Figure 3A:
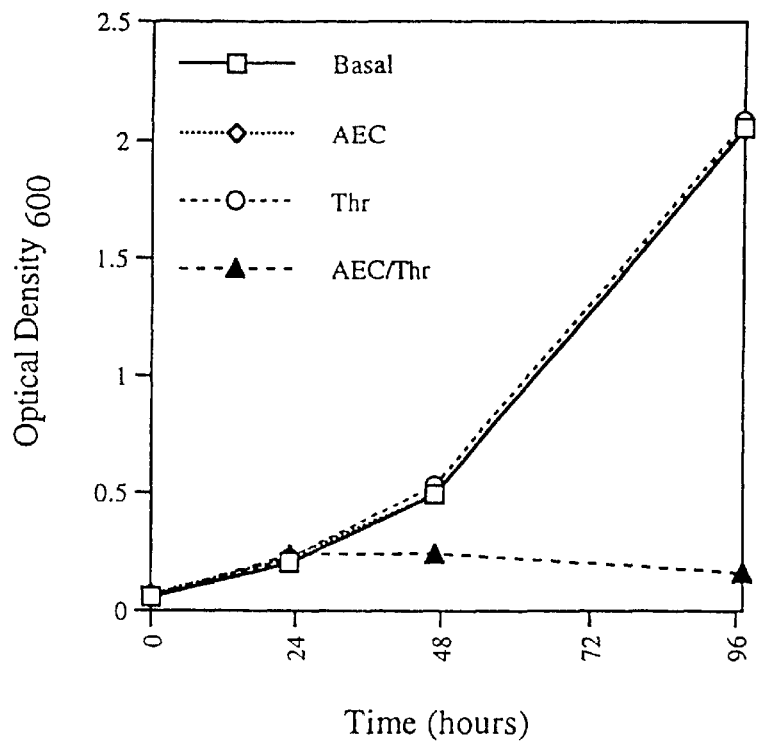
FIG. 3 illustrates the effect of AEC on the growth of wild-type *M. bovis* BCG, and *M. tuberculosis* H37Rv. Growth curve data were obtained as described in the Materials and Methods. Panel A illustrates growth of *M. bovis* BCG substrain Pasteur; Panel B illustrates growth of *M. tuberculosis* H37Rv. (Key: Basal (7H9 medium), AEC (Basal with 3 mM AEC), Thr (Basal with 3 mM threonine), AEC/Thr (Basal with AEC and threonine at 3 mM each.)
Figure 3B:
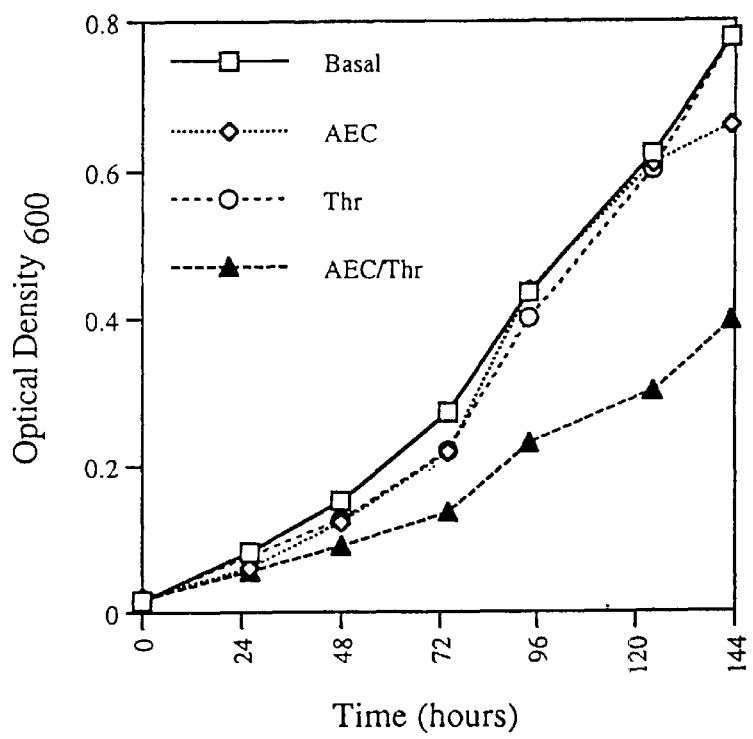

To include more DNA on both sides of the M. tuberculosis ΔlysA construct, cosmid cosY373 from the Sanger Centre M. tuberculosis H37Rv genome sequencing project (12) was used. An 11-kb SnaBI fragment from cosY373, containing lysA situated in the middle, was subcloned into the EcoRV site of pKSI$^+$ to yield plasmid pYUB659. To replace the wild-type lysA allele in pYUB659 with the ΔlysA::res-aph-res allele constructed above in pYUB638, the inventors exchanged an internal NheI-BglII fragment of lysA encompassing the deletion region between these two plasmids. Because there is an additional NheI site at the 5' end of the res-aph-res cassette, this exchange resulted in an additional deletion of 236-bp within the lysA gene. The resulting plasmid, pYUB665, contains a deletion within lysA totaling 331-bp and the res-aph-res cassette. Plasmid pYUB665 was passaged in *E. coli* DH5α (which has a γδ element capable of excising the aph gene from the ΔlysA::res-aph-res allele) and isolated a Kn$^s$ derivative, plasmid pYUB667. DNA sequence analysis of pYUB667 showed that the aph cassette was absent and a single res site remained that was in-frame with respect to the lysA open reading frame. The mutant lysA allele in pYUB667 is designated ΔlysA5::res and has a total deletion of 331-bp of an internal portion of the lysA gene, but with the addition of the 136-bp res site, the net change in size of ΔlysA5::res compared to wild-type is a decrease of 195-bp. To produce the final suicidal plasmid for allelic exchange in *M. bovis* BCG and *M. tuberculosis*, a 8.4-kb HpaI fragment from pYUB667 was cloned into the PacI sites of the sacB suicidal vector pYUB657, resulting in plasmid pYUB668. This plasmid has approximately 4-kb of DNA flanking each side of the ΔlysA5::res allele.

Electroporation of mycobacteria: *M. smegmatis* was electroporated as previously described (37). *M. bovis* BCG and *M. tuberculosis* were electroporated as per *M. smegmatis*, except that all manipulations were done at room temperature instead of on ice and the expression step proceeded overnight for approximately 12 hours prior to plating.

Nucleotide sequence accession number: The DNA sequence of the 4462 bp EcoRI fragment encoding the *M. smegmatis* lysA gene was submitted to GenBank and assigned the accession number AF126720.

B) Results

Allelic exchange methodology: The basic procedure for making mutants with the sacB suicidal vector pYUB657 (FIG. 1) is a two-step allelic exchange (15) (38). A suicidal recombination plasmid is electroporated into cells and primary recombinants selected upon hygromycin medium. Since the plasmid cannot replicate, any hygromycin resistant clones must have integrated the plasmid into the chromosome by a single crossover event. Because of the presence of the sacB gene on the pYUB657 vector backbone, the $Hyg^r$ clones are also sensitive to sucrose ($Suc^s$). Plasmid integration at the desired locus results in a tandem duplication (given the designation DUP) of the cloned region with the vector DNA in the middle. One such DUP clone is grown to saturation in supplemented medium, during which time individuals within the population undergo a second homologous recombination event between the duplicated regions. In this event, the plasmid vector loops out and is lost along with the hyg and sacB genes, leaving behind either the wild-type or mutant allele, depending upon which side of the mutation the second recombination event occurred. This second recombination event occurs at a low frequency, thus there must be a selection for the desired secondary recombinants. To select these clones one takes advantage of the loss of the sacB gene; any clone losing the plasmid is now sucrose resistant ($Suc^r$). The culture is plated on supplemented media containing sucrose to kill any clones that did not undergo a second recombination event. The sucrose resistant clones are then screened for hygromycin sensitivity and the mutant phenotype.

Cloning of the mycobacterial lysA genes: The present system by constructing lysine auxotrophs via deletion of the lysA gene, encoding meso-diaminopimelate decarboxylase, in *M. smegmatis, M. bovis* BCG, and *M. tuberculosis*. The lysA gene of *M. tuberculosis* was already available and could also be used for allelic exchange in *M. bovis* BCG due to the conservation of DNA sequences between the two species, however, the lysA gene of *M. smegmatis* was not available. The *M. smegmatis* lysA gene and resident operon was cloned as described in the Materials and Methods. The lysA gene of *M. smegmatis* is 1424-bp in length and shares 77% homology with the lysA gene of *M. tuberculosis*, while the two LysA proteins share a 80% identity (17). The structure of the lysA operon is conserved between several mycobacteria and the related organism *Corynebacterium glutamicum*. In *M. tuberculosis*, the gene order is: argS (arginyl-tRNA synthetase), lysA(meso-DAP decarboxylase), hdh (homoserine dehydrogenase), thrC (threonine synthase), PGRS-17 (poly GC-rich repeat 17), and thrB (threonine kinase) (http). The sequence from *M. smegmatis* spans upstream of args through the hdh gene. A similar argS-lysA operon arrangement is seen for *M. leprae* (37) and *Brevibacterium glutamicum* (renamed *Corynebacterium glutamicum)* (35). The hdh gene product supplies homoserine, the precursor for Met and Thr biosynthesis (30); while the thrC and thrB genes are responsible for threonine synthesis (36).

Construction of an unmarked lysA deletion mutant of *M. smegmatis: M. smegmatis* $mc^2155$ was electroporated with the ΔlysA4 suicidal plasmid pYUB618 (see Materials and Methods for plasmid construction) and obtained an average of 15 $Hyg^r$ clones per transformation, with primary recombination efficiencies of $10^{-5}$ (see Table 3). Two cultures of one strain, $mc^2 1492$, were grown to saturation in 7H9/lysine media and dilutions plated onto 7H10/lysine medium supplemented with sucrose. Sucrose resistant clones were obtained at a frequency of $10^{-4}$, and 100 clones from each set were screened for $Suc^r$, $Hyg^s$, and auxotrophy. Three basic phenotypes were found: $Suc^r$/$Hyg^r$/prototrophic, $Suc^r$/$Hyg^s$/prototrophic, and $Suc^r$/$Hyg^s$/auxotrophic (see Table 4, exps. 1 and 2). The largest group was the $Suc^r$/$Hyg^r$/prototrophic class and likely resulted from inactivation of the sacB gene, since the clones were still resistant to hygromycin and did not appear to have arisen from a secondary recombination event. The other two $Suc^r$ classes were $Hyg^s$ and appeared to result from secondary recombination events; the first class retained the wild-type allele, while the second class retained the mutant allele and were auxotrophic for lysine. One mutant was given the designation $mc^2 1493$ and allelic exchange of lysA confirmed by Southern blot (see FIG. 2, panel A). The mutant grows equally well on defined 7H9 medium supplemented with lysine or on complex media (7H9 supplemented with casamino acids or LB medium).

Construction of an unmarked lysA deletion mutant of *M. bovis* BCG substrain Pasteur: The suicide plasmid pYUB668 (see Materials and Methods) was used to construct an unmarked, in-frame deletion of lysA (ΔlysA5::res) in the genome of *M. bovis* BCG substrain Pasteur. After electroporation of BCG substrain Pasteur with the suicide plasmid, an average of 5 $Hyg^r$ clones were obtained per transformation with a primary recombination efficiency of $10^{-4}$ (see Table 3). Several $Hyg^r$, $Suc^s$ clones were screened by PCR to determine which of the primary clones were homologous recombinants. Three out of four clones examined had incorporated the suicide plasmid pYUB668 at the lysA locus, while the fourth appeared to be the result of an illegitimate recombination event (data not shown). Two clones were chosen for further study, $mc^2 1601$ (DUP3) and $mc^2 1602$ (DUP4) both of which had integrated pYUB668 at lysA but had differed in the orientation of the duplication (see Table 1). The two strains were grown to saturation in 7H9 media supplemented with lysine, methionine, and threonine and then plated upon the same type of media containing sucrose. This combination of amino acids was used to ensure that any unforeseen polar effect of the ΔlysA5::res allele on the downstream Met and Thr biosynthetic genes would not prevent the isolation of mutants. The results of the sucrose selection are shown in Table 4, exp 3 and 4. Suc$^r$ clones were obtained at a frequency of $10^{-4}$ and observed the same three classes of secondary recombinants that we saw in the *M. smegmatis* experiments. Allelic exchange was confirmed in strain mc$^2$1604, a mutant derived from DUP3 strain mc$^2$1601 (see Southern blot, FIG. 2, panel B). The auxotroph mc$^2$1604 does not revert, and no suppression was observed in two independent cultures of $5 \times 10^9$ CFU each.

The kinetics of allelic exchange of lysA in *M. bovis* BCG substrain Pasteur was surprisingly similar to that of *M. smegmatis* prompting examination of the reproducibility of this system. Sucrose selection was repeated with *M. bovis* BCG substrain Pasteur DUP3 strain $mc^2$1601 using cultures grown in Basal medium or media supplemented with Lys, Met+Thr+Lys, or casamino acids (acid-hydrolyzed casein). $Suc^r$ clones were obtained from each of the respective cultures at a frequency similar to those seen in the previous experiment with $mc^2$1601 (See Table 4, exps. 5 through 8, compare to exp. 3). The distribution of the three phenotypic classes in the $Suc^r$ population was also similar except that no lysine auxotrophs were obtained from cultures grown in Basal medium lacking lysine (as expected) or, surprisingly, casamino acids medium (Table 4, exps. 5 and 8).

Using allelic exchange to distinguish homologous from illegitimate primary recombinants: When using the two-step allelic exchange methodology with the slow-growing mycobacteria, it is important to identify primary recombinants that resulted from illegitimate recombination and those which resulted from homologous recombination. This can be done by PCR screening (as we did for the above experiment) or Southern blot, although these screening methods are difficult when using large recombination substrates. The inventors reasoned it should be possible to distinguish between the two types of recombinants by observing the phenotypic frequencies in the pool of $Suc^r$ secondary clones. Presumably, any primary recombinant resulting from a homologous integration of the plasmid at lysA would be able to undergo a second recombination event and loop out the plasmid, while a recombinant that had integrated the plasmid via illegitimate recombination would be unable to do the same. Any $Suc^r$ clones arising from an illegitimate recombinant would result from inactivation of the sacB gene as seen above and all these clones should also be $Hyg^r$.

This idea was tested in a series of lysA allelic exchange experiments with BCG substrain Connaught. Electroporation of BCG Connaught with the suicide plasmid pYUB668, yielded an average of 2 $Hyg^r$ clones per electroporation for a primary recombination efficiency of $10^{-3}$ (see Table 4). 7 Hyg, $Suc^s$ BCG Connaught::pYUB668 primary recombinants were chosen, grown in media supplemented with lysine and plated for sucrose resistant clones. The $Suc^r$ clones were screened for hygromycin sensitivity and auxotrophy (see Table 4, exps 9 through 15). Three of the seven primary recombinants (clones 3, 9, and 10) gave rise to similar phenotypic populations as that seen for *M. bovis* BCG substrain Pasteur DUP strains $mc^2$1601 and $mc^2$1602 (compare results in Table 4). Therefore, these three primary clones (3, 9, and 10) were homologous primary recombinants. Two clones (2 and 11) yielded only $Suc^r$, $Hyg^r$, prototrophs, while the remaining clones (4 and 8) yielded a majority of $Suc^r$, $Hyg^r$, prototrophs and a small number of $Suc^r$,$Hyg^s$, prototrophs (Table 4). These four primary clones (2, 4, 8, and 11) were classified as illegitimate recombinants. One BCG substrain Connaught lysine auxotroph, derived from clone 3 was designated strain $mc^2$2519, and allelic exchange confirmed by Southern blot (see FIG. 2, panel B).

Construction of an unmarked, in-frame lysA deletion mutant of *M. tuberculosis* strain H37Rv: The same methodology and suicide plasmid, pYUB668, described above was used to construct a lysA deletion mutant of *M. tuberculosis* H37Rv. Primary recombination efficiencies were observed that were similar to those observed in experiments with BCG substrain Pasteur (see Table 3). Six $Hyg^r$, $Suc^s$ primary recombinants were chosen, grown in lysine supplemented medium and plated for sucrose resistant recombinants. All 6 primary recombinants gave rise to phenotypic populations similar to the results seen with the BCG $mc^2$1601 DUP3 strain grown in Basal medium in Table 4, exp. 5 (data not shown). It was concluded that these primary clones were all likely homologous recombinants, but that something was wrong with the system since we did not isolate any auxotrophs. The sucrose selection was repeated with two of these primary recombinant strains, $mc^2$2998 and $mc^2$2999, grown in several types of media: Basal, Lys, Met+Thr+Lys, and casamino acid (see Table 4, exps. 16 through 23). The frequency of sucrose resistance was in the range of $10^{-5}$ to $10^4$ (see Table 4). Again, auxotrophs were not obtained and it was confirmed that the phenotypic frequencies within the $Suc^r$ population were similar to the failure to isolate Lys-BCG mutants on Basal medium (compare Table 4, exps. 17 and 18 with exp. 5). Furthermore, the results from the *M. tuberculosis* primary recombinants were unlike the results obtained with the BCG Connaught illegitimate primary recombinants. Thus, these results suggested that the primary recombinants were indeed homologous, but for some reason any auxotrophs resulting from a secondary recombination event were nonviable. Apparently, the media could not support the growth of a *M. tuberculosis* lysine auxotroph. It was decided to determine if the inability to isolate a lysine auxotroph of *M. tuberculosis* was due to the inability of the organism to transport lysine.

Transport of lysine in mycobacteria: To investigate lysine transport in *M. tuberculosis*, the toxic lysine analog S-(β-aminoethyl)-L-cysteine (AEC) was used. AEC is transported via lysine importers; the lysine permeases of *E. coli* (LysP), and *Corynebacterium glutamicum* (LysI) were identified using AEC-resistant mutants (46, 49). AEC inhibits aspartokinase, the enzyme catalyzing the first step of the aspartate amino acid family pathway responsible for the synthesis of Met, Thr, Ile, Lys, and DAP (meso-diaminopimelate), the latter begin a component of the cell envelope peptidoglycan and the precursor to lysine (45) (24). AEC alone is capable of inhibiting the growth of *E. coli*, but requires the addition of threonine to inhibit the growth of *C. glutamicum* (45). Presumably, full AEC sensitivity in corynebacteria requires repression of the threonine branch of the pathway by threonine.

The growth curves of *M. tuberculosis* strain H37Rv and BCG substrain Pasteur in media with or without AEC and Thr are shown in FIG. 3. A molar concentration of 3 mM was used for AEC and Thr, a concentration that is close to the 40 μg/ml used for amino acid supplementation in the inventors' studies. As seen in FIG. 3, panels A and B, neither AEC or Thr alone have an inhibitory effect upon the growth of the two species, however the combination of the two does inhibit growth, with BCG experiencing the greatest inhibition compared to *M. tuberculosis*. One interpretation of the results of this experiment is that lysine uptake is not as efficient in *M. tuberculosis* compared to BCG. The BCG lysine auxotrophic mutant mc²1604 does not grow well in media supplemented with lysine at concentrations below the standard concentration of 40 μg/ml (data not shown). This suggests that a decrease in transport efficiency of *M. tuberculosis* compared to that of BCG might preclude isolation of a *M. tuberculosis* lysine auxotroph. Since the inability to isolate a lysine auxotroph of *M. tuberculosis* might be due to inefficient lysine transport by the organism, another attempt was made using media with increased amounts of lysine.

Identification of media that support the growth of a *M. tuberculosis* H37Rv lysine auxotroph: Allelic exchange with the *M. tuberculosis* primary pYUB668 homologous primary recombinant strain $mc^2$2999 was repeated using modified media with increased amounts of lysine. Experiments utilizing media containing lysine at 200 μg/ml, or 200 μg/ml with 0.05% Tween-80, or lysine at 1 mg/ml did not yield any auxotrophs (Table 4, exps. 24–26). However, auxotrophic mutants were isolated when media containing lysine at 1 mg/ml with 0.05% Tween-80 was used (Table 4, exp. 27). The mutants produce colonies that are much smaller than wild-type and were easily identified on the sucrose selection plates (see Table 4, exp 27).

One mutant was designated $mc^2$3026 and allelic exchange of lysA was confirmed by Southern blot (see FIG. 2, Panel B). No reversion or suppression was seen in $3\times10^9$ CFU. The mutant grows slowly, requiring approximately 4–5 weeks to form a large colony on solid media and has an approximate doubling time of 48 hours in liquid medium (data not shown). Surprisingly, the mutant can grow on 7H10 solid media supplemented with casamino acids and also grows on 7H11 (supplemented with casitone, a pancreatic digest of casein), but requires high concentrations of lysine if lysine is the sole supplementation. It has an absolute dependency upon Tween-80 regardless of the type of solid media.

C) Discussion

Several groups have demonstrated the use of suicide plasmids for allelic exchange in fast and slow-growing mycobacteria. The most efficient are those systems using a counter selectable marker; for mycobacteria, workers have successfully used rpsL (37, 44), pyrF (27), and sacB (42). The most promising counter selectable system for the slow-growing mycobacteria is sacB, which confers sensitivity to sucrose. Methodologies using sacB were used for the targeted disruptions of ureC in BCG (42) and *M. tuberculosis* (39); and the erp gene of BCG and *M. tuberculosis* (9).

It was decided to construct a new sacB suicidal vector, pYUB657, and test it for the construction of unmarked, in-frame deletion mutants in the slow-growing mycobacteria. These studies provided an opportunity to examine homologous recombination in the mycobacteria from a practical standpoint. The bane of allelic exchange in slow-growing mycobacteria has been the propensity with which these organisms incorporate exogenous DNA into their genome via illegitimate recombination (25) (2, 32). Allelic exchange in *M. smegmatis* is relatively easy, and this species does not appear integrate DNA via illegitimate recombination. Several workers have suggested that the homologous recombination machinery is rather inefficient in the slow-growing mycobacteria. It is generally believed that illegitimate recombination occurs at a higher frequency than homologous recombination in the slow-growing mycobacteria, but this does not necessarily mean that homologous recombination is defective in these organisms (32).

In any allelic exchange technique with the slow-growing mycobacteria, it is important to distinguish homologous primary recombinants from illegitimate recombinants; in a method of the present invention, this was done by observing the frequencies of the phenotypes in the $Suc^r$ populations. The inventors's experiments with BCG substrain Connaught and *M. tuberculosis* pYUB668 recombinants showed that one using the present method could reproducibly determine if they had a primary homologous recombinant, obtain the mutant or discover that the mutation was not permitted, all at once. The illegitimate pYUB668 recombinants of BCG substrain Connaught were apparently unable to undergo a second recombination event, since virtually all of the $Suc^r$ clones were sacB inactivated clones. A small number of $Suc^r$ $Hyg^r$ clones from Connaught::pYUB668 clones 4 and 8 may have arisen from deletions within the integrated plasmid.

The results of this work suggest that homologous recombination in *M. bovis* BCG and *M. tuberculosis* is as efficient as that in *M. smegmatis*. First, the frequency of integration of suicidal plasmids into the chromosomes of the fast and slow-growers is similar, within the $10^{-4}$ to $10^{-5}$ range (except for BCG-Connaught which was $10^{-3}$; this might be an inflated value however, due to an unusually low electroporation efficiency with the control vector pYUB412). While the number of primary recombinants obtained in BCG and *M. tuberculosis* is often less than that obtained in *M. smegmatis*, the differences in the number of primary recombinants and recombination frequencies are small, and the electroporation frequencies are at best, only an approximation. It is suspected that any significant differences in primary recombination frequencies between slow-growers and *M. smegmatis* likely reflect a difference in DNA entry into the cells, since it is generally agreed that higher electroporation efficiencies are possible with *M. smegmatis* than with the slow-growers.

The recombination frequencies for the slow-growing mycobacteria includes both homologous and illegitimate recombinants, thus a direct comparison between the frequencies of primary recombination in fast and slow-growing mycobacteria may not be valid. However, more illegitimate recombination may occur with linear DNA than that which occurs with plasmid DNA. Electroporation of digested, linear insert DNA from the recombination plasmids of the present invention into BCG yielded 10 fold more clones than electroporation with the plasmids, but all clones were illegitimate recombinants (data not shown). In addition, we rarely obtained hygromycin resistant clones were rarely obtained when the sacB suicide vector pYUB657 lacking a DNA insert for recombination was electroporated into BCG or *M. tuberculosis* (data not shown).

Comparing homologous recombination frequencies among these three species is more straightforward when one examines the frequencies of secondary recombination events. When cultures were subjected to sucrose selection, sucrose resistant clones were obtained in the range of $10^{-4}$ to $10^{-5}$ for all three species, the same as the frequency seen for the primary recombination of the plasmid into the chromosome. In the sucrose resistant population, three phenotypic classes were observed, two of which resulted from a recombination event and one that the inventors believe did not. The latter class, the $Suc^r$, $Hyg^r$ prototrophs were designated "sacB inactivated" clones, since they were still hygromycin resistant. Inactivation of sacB at a similar frequency to that observed in this study has been noted previously (42). Counter-screenable markers can be inactivated at an approximate frequency of $10^{-5}$ in *M. smegmatis* by the action of mobile insertion elements (11). A similar phenomenon, at a lower frequency, has been seen using the rpsL system for allelic exchange in *M. smegmatis* (37).

In this study, mutants were constructed with a deletion in lysA, conferring a lysine auxotrophic phenotype. Unexpectedly, the lysine auxotrophs described herein have different lysine requirements. The *M. smegmatis* mutant is the most flexible in its requirements, growing on chemically defined media supplemented with lysine as well as medium supplemented with casamino acids. In contrast, auxotrophs of BCG Pasteur could not be isolated using casamino acids-containing media, even though the compositional analysis of the casamino acids used in this study showed that the media should have a lysine concentration that is threefold greater than the amount required for the BCG lysine auxotrophs (13). Neither the BCG Pasteur or Connaught lysine auxotrophs are able to grow on solid media if casamino acids or casitone (a pancreatic digest of casein) is used as the source of lysine. Previously studied Met, Ile-Val, and Leu auxotrophic mutants of BCG can grow on all of these media, unlike the BCG lysine auxotrophs described in this study (31) (25). In more recent work with transposon mutagenesis of BCG; there were attempts to assay the efficiency of mutagenesis by screening for amino acid auxotrophy (7). The only mutants that were obtained were Leu auxotrophs, as isolated previously. This led to some concern that the transposition mechanism might not be random which would be detrimental to a mutagenesis system (6). However, all of these attempts utilized media containing casein preparations. Under such conditions, lysine auxotrophs would not be isolated. It is possible that the casein phenomenon described here is more widespread and could explain the dearth of auxotrophs in the above experiments. The inventors are currently investigating why the BCG lysine auxotrophs fail to grow on media containing casein.

Lysine auxotrophs of *M. tuberculosis* H37Rv were not isolated until media with a high concentration of lysine and 0.05% Tween-80 was used. As in the case for BCG, *M. tuberculosis* mutants could not be isloated using casamino acids, however, once a mutant was obtained, the inventors found that it could grow on casamino acids media or casitone, as long as there was Tween-80 in the media. Since the *M. tuberculosis* mutant is dependent upon the presence of Tween-80, the inventors assume that the failure to obtain a mutant using casamino acids media was due to the absence of Tween in the selection media. It is important to note that Tween-80 does not allow the BCG auxotrophs to form colonies of casamino acids media. Based upon the AEC toxicity data, it can be concluded that *M. tuberculosis* H37Rv does not transport lysine as effectively as BCG. Alternatively, since AEC toxicity requires transport of threonine as well, the AEC results could be explained by inefficient threonine transport. However, the high lysine requirement of the mutant and the dependency upon Tween-80 would support the former conclusion, since Tween-80 is believed to increase the permeability of the mycobacteria cell envelope (21). The primary phenotypic difference between the BCG and the *M. tuberculosis* mutants is that the BCG mutants require lysine supplementation alone, while the *M. tuberculosis* mutant requires Tween-80 along with either lysine at high concentration or casamino acids.

The auxotrophic mutants obtained herein will be useful in a variety of applications. The BCG and *M. tuberculosis* lysine mutants may be usable for the construction of DAP auxotrophs (peptidoglycan mutants), as the inventors have done for *M. smegmatis* (37). A series of vectors bearing the lysA gene are also being developed that could be used for the expression of foreign antigens in the BCG auxotrophs; the presence of the lysA gene would maintain the plasmids in vivo in the absence of antibiotic selection. The behavior of the BCG mutants in animals is being tested in the hope that they could be used in HIV infected populations as a safer alternative to live, wild-type BCG vaccine. One major goal of mycobacterial research is the development of attenuated strains of *M. tuberculosis* that could be used as potential vaccine strains. Such mutant strains would be unable to grow in a host, or grow only for a short time, lasting long enough to prime the immune system. To this end, the inventors are currently examining the growth kinetics of the *M. tuberculosis* auxotroph in animal models.

TABLE 1

Strains used in this study

| Strain | Description | Reference |
|---|---|---|
| *E.coli* K-12 | | |
| HB101 | F- Δ(gpt-proA)62 leuB1 glnV44 ara-14 lacY1 hsdS20 rpsL20 xyl-5 mtl-1 recA13 | (10) |
| DH5α | F- [φ80dΔlacZM15]Δ(lacZYA-argF)U169 deoR recA1 endA1 hsdR17 glnV44 thi-1 gyrA96 relA1 | (19) |
| *M. smegmatis* | | |
| mc$^2$155 | ept-1 | (47) |
| mc$^2$1492 | ept-1 DUP2 [(argS ΔlysA4 hdh')*pYUB657*(argS lysA hdh)] | This work |
| mc$^2$1493 | ept-1 ΔlysA4 | This work |
| *M. bovis* BCG | | |
| Pasteur | Vaccine strain | Statens Seruminstitut |
| mc$^2$1601 | Pasteur DUP3 [(argS lysA hdh thrC)*pYUB657*(argS ΔlysA5::res hdh thrC')] | This work |
| mc$^2$1602 | Pasteur DUP4 [(argS ΔlysA5::res hdh thrC)*pYUB657*(argS lysA hdh thrC)] | This work |
| mc$^2$1604 | Pasteur ΔlysAS::res | This work |
| Connaught | Vaccine strain | AECOM |
| mc$^2$1618 | Connaught::pYUB668 homologous primary recombinant, clone 3 | This work |
| mc$^2$2519 | Connaught ΔlysA5::res | This work |
| *M. tuberculosis* H37Rv | Virulent | AECOM |
| mc$^2$2998 | H37Rv::pYUB668 homologous primary recombinant, clone 1 | This work |
| mc$^2$2999 | H37Rv::pYUB668 homologous primary recombinant, clone 2 | This work |
| mc$^2$3026 | ΔlysA5::res | This work |

| Name | Description | Reference |
|---|---|---|
| pKSI+ | Ap$^r$, high copy number cloning vector | Stratagene |
| pMV261 | Km$^r$, E. coli-mycobacterial shuttle vector | (51) |
| pET3d.lysA | M. tuberculosis Erdman lysA gene cloned into pET3d | (16) |
| pCVD442 | Ap$^r$, sacB | (15) |
| pYUB328 | Ap$^r$, PacI-excisable cosmid vector, ColE1 | (5) |
| pYUB405 | Ap$^r$, Hyg$^r$, PacI-excisable cosmid vector, ColE1, does not replicate in mycobacteria | (6) |
| pYUB412 | Ap$^r$, Hyg$^r$, E. coli-mycobacteria shuttle PacI-excisable cosmid vector, ColE1 origin, int attP, nonreplicative but integration proficient in mycobacteria | (6) |
| pYUB601 | in vitro repackaged pYUB412::lysA$^+$ cosmid from mc$^2$155 library | This work |
| pYUB604 | 4.4-kb EcoRI fragment from pYUB601 cloned in the EcoRI site of pMV261 | This work |
| pYUB605 | 5.5-kb NotI self-ligated subclone of pYUB6O4 | This work |
| pYUB607 | 3.4-kb NotI fragment from pYUB604 cloned into NotI site of pKSI+ | This work |
| pYUB617 | 7.7-kb inverse XL-PCR product from pYUB604, containing a 1.2-kb deletion of lysA (ΔlysA4) marked with unique SnaBI site. | This work |
| pYUB618 | 3.2-kb EcoRI fragment from pYUB617, bearing ΔlysA4, blunt cloned into PacI sites of pYUB657 | This work |
| pYUB631 | 2.5-kb PstI fragment from pCVD442, bearing sacB, cloned into same of pMV261 | This work |
| pYUB635 | 1.3-kb XbaI-BamHI lysA gene from pET3d.lysA, cloned into same sites of pKSI+ | This work |
| pYUB636 | 3-kb inverse XL-PCR product from pYUB635, containing 95-bp deletion of lysA marked with unique MluI site | This work |
| pYUB638 | 1.4-kb MluI res-aph-res cassette cloned into MluI site in pYUB636 | This work |
| pYUB651 | pYUB412 containing lysA$^+$ of M. tuberculosis Erdman, under control of the BCG groEL (Hsp60) promoter | |
| pYUB657 | 3.5-kb NotI-NheI fragment from pYUB631, bearing groEL (Hsp60) promoter and sacB, cloned into the EcoRV site of pYUB405 | This work |
| pYUB659 | 11-kb SnaBI fragment from cosY373 cloned into the EcoRV site of pKSI+ | This work |
| pYUB665 | 1.7-kb NheI-Bg/II fragment from pYUB638 (ΔlysA::res-aph-res) replacing 300 bp NheI-Bg/II (lysA$^+$) fragment in pYUB659 | This work |
| pYUB667 | pYUB665 with the aph gene resolved by passage in E. coli DH5α, Km$^s$ | This work |
| pYUB668 | 8.4-kb HpaI fragment from pYUB667 cloned into the PacI sites of pYUB657 | This work |
| cosY373 | pYUB382::M. tuberculosis H37Rv cosmid bearing the lysA operon | (1) |

TABLE 3

Electroporation efficiencies and primary recombination frequencies for lysA allelic exchange

| Species/strain | Suicide plasmid | (N)$^a$ | Ave. # Hyg$^r$ clones$^b$ | Electroporation efficiency$^c$ | Recombination frequency$^d$ |
|---|---|---|---|---|---|
| M. smegmatis mc$^2$155 | pYUB618 | 2 | 15 ± 3 | 3 × 10$^5$ | 5 × 10$^{-5}$ |
| M. bovis BCG-Pasteur | pYUB668 | 10 | 5 ± 3 | 1 × 10$^4$ | 5 × 10$^{-4}$ |
| M. bovis BCG-Connaught | pYUB668 | 5 | 2 ± 1 | 1 × 10$^3$ | 2 × 10$^{-3}$ |
| M. tuberculosis H37Rv | pYUB668 | 10 | 3 ± 3 | 3 × 10$^5$ | 1 × 10$^{-5}$ |

$^a$(N) = number of electroporations for each species/plasmid combination. Each set was done with the same stock of electrocompetent cells.
$^b$Average number of Hygromycin resistant clones (± standard deviation) from each set of etectroporations done with the suicide plasmids.
$^c$Electroporation efficiency is the number of Hyg$^r$ clones obtained from electroporations done with pYUB412, an attP/int Hyg$^r$vector that integrates into the attB site of the mycobacterial genome. The number of Hyg$^r$ clones from pYUB412 electroporations is an indicator of the electroporation efficiency of the cells; the number of transformants obtained with an attP/int vector is equivalent to the number obtained with a replicating vector. We have never observed spontaneous resistance to hygromycin in the species studied in this paper.
$^d$Recombination frequency is calculated by dividing the average number of Hyg$^r$ clones obtained per electroporation with suicide plasmids, divided by the electroporation efficiency obtained with the vector pYUB412.

TABLE 4

Recombination products from segregation of lysA DUP in different mycobacterial species

| | | | | | | | Frequency of phenotypes in Suc$^r$ population[e] | | |
| | | | | | | | (sacB inactivated) | (secondary recombinants) | |
| Species | Exp | Strain | Relevant genotype[a] | Media[b] | Suc$^r$ freq.[c] | (N)$_d$ | Hyg$^r$ prototrophs | Hyg$^s$ prototrophs | Hyg$^s$ auxotrophs |
|---|---|---|---|---|---|---|---|---|---|
| *M smegmatis* | 1 | mc²1492 | DUP2 | K | 4 | 100 | 67 | 24 | 9 |
| | 2 | mc²1492 | | K | 3 | 100 | 60 | 31 | 9 |
| *M. bovis* BCG | 3 | mc²1601 | DUP3 | K,M,T | 4 | 48 | 2 | 63 | 35 |
| Pasteur | 4 | mc²1602 | DUP4 | K, M, T | 9 | 46 | 26 | 33 | 41 |
| | 5 | mc²1601 | DUP3 | Basal | 0.2 | 92 | 9 | 91 | 0 |
| | 6 | mc²1601 | | K | 0.9 | 86 | 15 | 73 | 12 |
| | 7 | mc²1601 | | K, M, T | 3 | 90 | 11 | 61 | 28 |
| | 8 | mc²1601 | | CAA | 6 | 78 | 8 | 92 | 0 |
| Connaught | 9 | clone 3 | Hom. pYUB688 | K | N.D. | 47 | 15 | 51 | 34 |
| | 10 | clone 9 | " | K | N.D. | 48 | 6 | 54 | 40 |
| | 11 | clone 10 | " | K | N.D. | 47 | 10 | 77 | 13 |
| | 12 | clone 2 | Illeg. pYUB668 | K | N.D. | 48 | 100 | 0 | 0 |
| | 13 | clone 4 | " | K | N.D. | 48 | 96 | 4 | 0 |
| | 14 | clone 8 | " | K | N.D. | 47 | 98 | 2 | 0 |
| | 15 | clone 11 | " | K | N.D. | 95 | 100 | 0 | 0 |
| *M. tuberculosis* | 17 | mc²2998 | | K | 0.3 | 41 | 10 | 90 | 0 |
| | 18 | mc²2998 | | K, M, T | 1 | 45 | 16 | 84 | 0 |
| | 19 | mc²2998 | | CAA | 0.6 | 40 | 23 | 77 | 0 |
| | 20 | mc²2999 | Hom. pYUB688 | Basal | 0.5 | 42 | 26 | 74 | 0 |
| | 21 | mc²2999 | | K | 0.9 | 38 | 13 | 87 | 0 |
| | 22 | mc²2999 | | K, M, T | 2 | 44 | 36 | 64 | 0 |
| | 23 | mc²2999 | | CAA (a) | 0.7 | 34 | 6 | 94 | 0 |
| | 24 | mc²2998 | Hom. pYUB688 | K200 | 2 | 39 | 44 | 56 | 0 |
| | 25 | mc²2998 | | K200/TW | 10 | 287 | 20 | 80 | 0 |
| | 26 | mc²2998 | | K1 | 0.3 | 96 | 20 | 80 | 0 |
| | 27 | mc²2998 | | K1/TW | 1 L | 96L | 17L | 83L | 0L |
| | | | | | 0.8S | 63S | 0S | 0S | 100S |

[a]DUP designation is used for strains with pYUB688 integrated at lysA with known orientation (see Table 1). "Illeg. PYUB688" refers to primary Hyg$^r$ Suc$^s$ clones in which PYUB688 integrated into the chromosome via illegitimate recombination. "Hom. pYUB688" refers to primary Hyg$^r$ Suc$^s$ clones in which pYUB688 integrated at lysA but the orientation of the duplication is unknown.
[b]Type of media used for outgrowth (Middlebrook 7H9) and sucrose selection (Middlebrook 7H10): Basal (no supplementation), K (lysine @ 40 μg/ml), K, M, T (lysine, methionine, and threonine each @ 40 μg/ml), CAA (0.2% casamino acids, acid-hydrolyzed), K200 (lysine @ 200 μg/ml), K200/TW (lysine @ 200 μg/ml plus 0.05% Tween-80), K1 (lysine @ 1 mg/ml), K1/TW (lysine @ 1 mg/ml plus 0.05% Tween-80)
[c]Number of Suc$^r$ CFU/ml divided by the viable CFU/ml, (expressed as N × $10^{-4}$).
[d](N) = number of Suc$^r$ clones screened.
[e]Frequency of phenotypes expressed as a percentage of the number of sucrose resistant clones screened. Hyg$^r$ prototrophs (not secondary recombinants-"sacB inactivated"), Hyg$^s$ prototrophs (secondary recombinants, wild-type lysA), Hyg$^s$ auxotrophs (secondary recombinants, ΔlysA).
[f]For exp. number 27, "L" refers to large colonies, while "S" refers to small colonies seen on the sucrose selection medium.
N.D. (not determined)

References

1. *M. tuberculosis* H37Rv genome project, vol. 1999. The Sanger Centre.
2. Aldovini, A., R. N. Husson, and R. A. Young. 1993. The uraA locus and homologous recombination in *Mycobacterium bovis* BCG. Journal of Bacteriology. 175:7282–7289.
3. Andersen, Å. B., and E. B. Hansen. 1993. Cloning of the lysA gene from *Mycobacterium tuberculosis*. Gene. 124:105–109.
4. Azad, A. K., T. D. Sirakova, L. M. Rogers, and P. E. Kolattukudy. 1996. Targeted replacement of the mycocerosic acid synthase gene in *Mycobacterium bovis* BCG produces a mutant that lacks mycosides. Proc. Natl. Acad. Sci. USA. 93:4787–4792.
5. Balasubramanian, V., M. S. Pavelka Jr., S. S. Bardarov, J. Martin, T. R. Weisbrod, R .A. McAdam, B. R. Bloom, and W. R. Jacobs Jr. 1996. Allelic exchange in *Mycobacterium tuberculosis* with long linear recombination substrates. J. Bacteriol. 178:273–279.
6. Bardarov, S., and W. R. Jacobs Jr. 1995. Unpublished (personal communication).
7. Bardarov, S. B., J. Kriakov, C. Carriere, S. Yu, C. Vaamonde, R. McAdam, B. R. Bloom, G. F. Hatfull, and J. Jacobs, W. R. 1997. Conditionally replicating mycobacteriophages: A system for transposon delivery to *Mycobacterium tuberculosis*. Proc. Natl. Acd. Sci. USA. 94:10961–10966.
8. Bardarov, S. B., J. Pavelka, M. S., G. F. Hatfull, and J. Jacobs, W. R. 1996.
9. Berthet, F. X., M. Lagranderie, P. Gounon, C. Laurent-Winter, D. Ensergueix, P. Chavarot, F. Thouron, E. Maranghi, V. Pelicic, D. Portnoi, G. Marchal, and B. Gicquel. 1998. Attenuation of virulence by disruption of the *Mycobacterium tuberculosis* erp gene. Science. 282 (5389):759–62.
10. Boyer, H., and D. Roulland-Dussoin. 1969. A complementation analysis of the restriction and modification of DNA in *Escherichia coli*. J. Mol. Biol. 41:459–472.
11. Cirillo, J. D., R. G. Barletta, B. R. Bloom, and J. Jacobs, W. R. 1991. A novel transposon trap for mycobacteria: Isolation and characterization of IS1096. *J. Bacteriol.* 173:7772–7780.
12. Cole, S. T., R. Brosch, J. Parkhill, T. Garnier, C. Churcher, D. Harris, S. V. Gordon, K. Eiglmeier, S. Gas, C. E. Barry, 3rd, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, B. G. Barrell, and et al. 1998. Deciphering the biology of *Mycobacterium tuberculosis* from the complete genome sequence [see comments] [published erratum appears in Nature November 1998 12;396(6707):190]. Nature. 393(6685):537–44.

13. DIFCO-BRL. (personal communication)

14. Dolin, P. J., M. C. Raviglione, and A. Kochi. 1994. Global tuberculosis incidence and mortality during 1990–2000. Bull. World Health Organ. 72:213–220.

15. Donnenberg, M. S., and J. B. Kaper. 1991. Construction of an eae deletion mutant of enteropathogenic *Escherichia coli* by using a positive selection vector. Infection and Immunity. 59:4310–4317.

16. Erlich, J., and J. Blanchard. 1995. Unpublished.

17. Glynias, M. J. 1991. Geneworks version 2.0.

18. Haas, D. W., and R. M. Des Prez. 1994. Tuberculosis and acquired immunodeficiency syndrome: a historical perspective on recent developments. Amer. J. Med. 96:439–450.

19. Hanahan, D. 1983. Studies of transformation of *Escherichia coli* with plasmids. J. Mol. Biol. 166:557–580.

20. Hatfull, G. F., J. J. Salvo, E. E. Falvey, V. Rimphanitchayakit, and N. D. Grindley. 1988. Site-specific recombination by the gamma delta resolvase, p. 149–181. In A. J. Kingsman, K. F. Chater, and S. M. Kingsman (ed.), Transposition. Cambridge University Press.

21. Hui, J., N. Gordon, and R. Kajioka. 1977. Permeability barrier to rifampin in mycobacteria. Antimicrob. Agents Chemother. 11:773–779.

22. Ish-Horowicz, D., and J. F. Burke. 1981. Rapid and efficient cosmid cloning. Nucleic Acids Res. 9:2989–2998.

23. Jacobs Jr, W. R., G. V. Kalpana, J. D. Cirillo, L. Pascopella, R. A. Udani, W. D. Jones Jr., R. Barletta, and B. R. Bloom. 1991. Genetic systems for the mycobacteria. Methods Enzymol. 204:537–555.

24. Kalinowski, J., B. Bachmann, G. Theirbach, and A. P ühler. 1990. Apartokinase genes lysCα and lysCβ overlap and are adjacent to the aspartate β-semialdehyde dehydrogenase gene asd in *Corynebacterium glutamicum*. Mol. Gen. Genet. 224:317–324.

25. Kalpana, G. V., B. R. Bloom, and W. R. Jacobs Jr. 1991. Insertional Mutagenesis and Illegitimate Recombination in Mycobacteria. Proc. Natl. Acad. Sci. U.S.A. 88:5433–5437.

26. Kalpana, G. V., W. R. J. Jacobs, and B. B. R. 1990. Unpublished observation.

27. Knipfer, N., A. Seth, and T. E. Shrader. 1997. Unmarked gene integration into the chromosome of *Mycobacterium smegmatis* via precise replacement of the pyrF gene. Plasmid. 37(2):129–40.

28. Lee, M. H., L. Pascopella, W. R. Jacobs Jr., and G. F. Hatfull. 1991. Site-specific integration of mycobacteriophage L5: integration-proficient vectors for *Mycobacterium smegmatis*, BCG, and *M. tuberculosis*. Proc. Natl. Acad. Sci. 88:3111–3115.

29. Maniatis, T., E. F. Fritsch, and J. Sambrook. 1982. Molecular cloning: a laboratory manual. Cold Spring Harbor Laboratory, Cold Spring Harbor, N.Y.

30. Mateos, L. M., A. Pisabarro, M. Patek, M. Malumbres, C. Guerrero, B. J. Eikmanns, H. Sahm, and J. F. Martin. 1994. Transcriptional analysis and regulatory signals of the hom-thrB cluster of *Brevibacterium lactofermentum*. J Bacteriol. 176(23):7362–71.

31. McAdam, R. A., T. R. Weisbrod, J. Martin, J. D. Scuderi, A. M. Brown, J. D. Cirillo, B. R. Bloom, and W. R. Jacobs Jr. 1995. In vivo growth characteristics of leucine and methionine auxotrophic mutants of *Mycobacterium bovis* BCG generated by transposon mutagenesis. Inf. Imm. 63(3):1004–1012.

32. McFadden, J. 1996. Recombination in mycobacteria. Mol Microbiol. 21(2):205–11.

33. McKinney, J. D., F. C. Bange, and J. Jacobs, W. R. (personal communication).

34. Mitchell, C. and Bluom, B.R., (personal communication)

35. Oguiza, J. A., M. Malumbres, G. Eriani, A. Pisabarro, L. M. Mateos, F. Martin, and J. F. Martin. 1993. A gene encoding arginyl-tRNA synthetase is located in the upstream region of the lysA gene in *Brevobacterium lactofermentum*: regulation of argS-lysA cluster expression by arginine. J. Bacteriol. 175:7356–7362.

36. Patte, J.-C. 1996. Biosynthesis of threonine and lysine, p.528–541. In F. C. Neidhradt (ed.), *Escherichia coli* and *Salmonella typhimurium*. ASM press.

37. Pavelka, J., M. S., and J. Jacobs, W. R. 1996. Biosynthesis of diaminopimelate (DAP), the precursor of lysine and a component of the peptidoglycan, is an essential function of *Mycobacterium smegmatis*. J. Bacteriol. 178.

38. Pavelka, M. S., Jr., S. F. Hayes, and R. P. Silver. 1994. Characterization of KpsT, the ATP-binding component of the ABC-transporter involved with the export of capsular polysialic acid in *Escherichia coli* K1. J Biol Chem. 269(31):20149–58.

39. Pelicic, V., M. Jackson, J. M. Reyrat, W. R. Jacobs, Jr., B. Gicquel, and C. Guilhot. 1997. Efficient allelic exchange and transposon mutagenesis in *Mycobacterium tuberculosis*. Proc Natl Acad Sci USA. 94(20):10955–60.

40. Pelicic, V., J. M. Reyrat, and B. Gicquel. 1996. Expression of the *Bacillus subtilis* sacB gene confers sucrose sensitivity on mycobacteria. J Bacteriol. 178(4):1197–9.

41. Pelicic, V., J. M. Reyrat, and B. Gicquel. 1996. Generation of unmarked directed mutations in mycobacteria, using sucrose counter-selectable suicide vectors. Mol Microbiol. 20(5):919–25.

42. Pelicic, V., J. M. Reyrat, and B. Gicquel. 1996. Positive selection of allelic exchange mutants in *Mycobacterium bovis* BCG. FEMS Microbiol Lett. 144(2–3):161–6.

43. Reyrat, J.-M., F.-X. Berthet, and B. Gicquel. 1995. The urease locus of *Mycobacterium tuberculosis* and its utilization for the demonstration of allelic exchange in *Mycobacterium bovis* bacillus Calmette-Guérin. Proc. Natl. Acad. Sci. USA. 92:8768–8772.

44. Sander, P., A. Meier, and E. C. Böttger. 1995. rpsL+: a dominant selectable marker for gene replacement in mycobacteria. Mol. Microbiol. 16:991–1000.

45. Sano, K., and I. Shiio. 1970. Microbial production of L-lysine. III. Production of mutants resistant to S-(-2-aminoethyl)-L-cysteine. J. Gen. Appl. Microbiol. 16:373–391.

46. Seep-Feldhaus, A. H., J. Kalinowski, and A. Puhler. 1991. Molecular analysis of the *Corynebacterium glutamicum* lysI gene involved in lysine uptake. Mol Microbiol. 5(12):2995–3005.

47. Snapper, S. B., R. E. Melton, S. Mustafa, T. Kieser, and J. J. W. R. 1990. Isolation and characterization of efficient plasmid transformation mutants of *Mycobacterium smegmatis*. Molec. Microbiol. 4:1911–1919.

48. Snider, D. E., M. Raviglione, and A. Kochi. 1994. Global Burden of Tuberculosis, p. 3–11. In B. R. Bloom (ed.), Tuberculosis: pathogenesis, protection, and control. American Society for Microbiology Press, Washington, D.C.

49. Steffes, C., J. Ellis, J. Wu, and B. P. Rosen. 1992. The lysP gene encodes the lysine-specific permease. J Bacteriol. 174(10):3242–9.
50. Steinmetz, M., D. Le Coq, S. Aymerich, G. Gonzy-Treboul, and P. Gay. 1985. The DNA sequence of the gene for the secreted *Bacillus subtilis* enzyme levansucrase and its genetic control sites. Mol Gen Genetics. 200:220–228.
51. Stover, C. K., V. F. de la Cruz, T. R. Fuerst, J. E. Burlein, L. A. Benson, L. T. Bennett, G. P. Bansal, J. F. Young, M. H. Lee, G. F. Hatfull, S. B. Snapper, R. G. Barletta, J. Jacobs, W. R., and B. R. Bloom. 1991. New use of BCG for recombinant vaccines. *Nature.* 351:456–460.
52. Umbarger, H. E. 1978. Amino acid biosynthesis and its regulation. Ann. Rev. Biochem. 47:533–606.

All publications mentioned herein above are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A recombinant *M. tuberculosis* comprising a mycobacterial lysA gene containing an unmarked mutation introduced by allelic exchange, wherein the recombinant *M. tuberculosis* requires a medium containing polyoxyethylenesorbitan monooleate and lysine for growth.

2. The recombinant *M. tuberculosis* of claim 1, wherein the source of lysine is casamino acids or casitone.

3. A method for preparing a recombinant *M. tuberculosis* comprising:
   (a) introducing a suicide plasmid into a *M. tuberculosis*, said suicide plasmid comprising a selectable marker, a counterselectable marker, and an unmarked mutant mycobacterial lysA gene;
   (b) selecting for primary recombinants incorporating the selectable marker;
   (c) culturing the primary recombinants incorporating the selectable marker;
   (d) selecting for secondary recombinants that have lost the counterselectable marker; and
   (e) isolating the secondary recombinants comprising the desired unmarked mutant mycobacterial lysA gene to obtain said recombinant *M. tuberculosis*, wherein said recombinant *M. tuberculosis* requires a medium containing polyoxyethylenesorbitan monooleate and lysine for growth.

4. The method of claim 3, wherein the selectable marker confers antibiotic resistance and the counters electable marker is one of rpsL, pyrF, and sacB.

5. The method of claim 3, wherein the counterselectable marker is sacB.

6. The method of claim 3, wherein the source of lysine is casamino acids or casitone.

7. A recombinant *M. bovis* BCG comprising a mycobacterial lysA gene containing an unmarked mutation introduced by allelic exchange, wherein the recombinant *M. bovis* BCG grows on a medium containing lysine but does not grow on a medium containing casamino acids or casitone.

8. A method for preparing a recombinant *M. bovis* BCG comprising:
   (a) introducing a suicide plasmid into a *M. bovis* BCG, said suicide plasmid comprising a selectable marker, a counterselectable marker, and an unmarked mutant mycobacterial lysA gene;
   (b) selecting for primary recombinants incorporating the selectable marker;
   (c) culturing the primary recombinants incorporating the selectable marker;
   (d) selecting for secondary recombinants that have lost the counterselectable marker; and
   (e) isolating the secondary recombinants comprising the desired unmarked mutant mycobacterial lysA gene to obtain said recombinant *M. bovis* BCG, wherein said recombinant *M. bovis* BCG grows on a media containing lysine but does not grow on a media containing casamino acids or casitone.

9. The method of claim 8, wherein the selectable marker confers antibiotic resistance and the counterselectable marker is one of rpsL, pyrF, and sacB.

10. The method of claim 8, wherein the counterselectable marker is sacB.

\* \* \* \* \*

SEQUENCE LISTING

```
<160> NUMBER OF SEQ ID NOS: 4

<210> SEQ ID NO 1
<211> LENGTH: 28
<212> TYPE: DNA
<213> ORGANISM: artificial sequence
<220> FEATURE:
<221> NAME/KEY: primer_bind
<222> LOCATION: (1)..(28)
<223> OTHER INFORMATION: oligonucleotide primer used to construct
      suicide plasmid pYUB618

<400> SEQUENCE: 1
cccgtcgtac gtacgaacca ggttgcgc                                        28

<210> SEQ ID NO 2
<211> LENGTH: 28
<212> TYPE: DNA
<213> ORGANISM: artificial sequence
<220> FEATURE:
<221> NAME/KEY: primer_bind
<222> LOCATION: (1)..(28)
<223> OTHER INFORMATION: oligonucleotide primer used to construct
      suicide plasmid pYUB618

<400> SEQUENCE: 2
cgagtcgata cgtactgctg tgccgccc                                        28

<210> SEQ ID NO 3
<211> LENGTH: 31
<212> TYPE: DNA
<213> ORGANISM: artificial sequence
<220> FEATURE:
<221> NAME/KEY: primer_bind
<222> LOCATION: (1)..(31)
<223> OTHER INFORMATION: oligonucleotide primer used to construct
      suicide plasmid pYUB668

<400> SEQUENCE: 3
gatagcggtc acgcgtctcg tgcgcggtgg a                                    31

<210> SEQ ID NO 4
<211> LENGTH: 32
<212> TYPE: DNA
<213> ORGANISM: artificial sequence
<220> FEATURE:
<221> NAME/KEY: primer_bind
<222> LOCATION: (1)..(32)
<223> OTHER INFORMATION: oligonucleotide primer used to construct
      suicide plasmid pYUB668

<400> SEQUENCE: 4
tccgtacgat acgcgtcagc cacatcggtt cg                                   32
```